US011751850B2

(12) United States Patent
Morrise et al.

(10) Patent No.: US 11,751,850 B2
(45) Date of Patent: Sep. 12, 2023

(54) ULTRASOUND UNIFIED CONTRAST AND TIME GAIN COMPENSATION CONTROL

(71) Applicant: yoR Labs, Inc., Portland, OR (US)

(72) Inventors: Matthew C. Morrise, Portland, OR (US); Oliver C. Johnson-Terleski, Tualatin, OR (US)

(73) Assignee: yoR Labs, Inc., Beaverton, OR (US)

( * ) Notice: Subject to any disclaimer, the term of this patent is extended or adjusted under 35 U.S.C. 154(b) by 0 days.

(21) Appl. No.: 17/455,564

(22) Filed: Nov. 18, 2021

(65) Prior Publication Data

US 2022/0151591 A1     May 19, 2022

Related U.S. Application Data

(60) Provisional application No. 63/115,863, filed on Nov. 19, 2020.

(51) Int. Cl.
*A61B 8/00*     (2006.01)
(52) U.S. Cl.
CPC .............. *A61B 8/467* (2013.01); *A61B 8/465* (2013.01)
(58) Field of Classification Search
CPC ......... A61B 8/467; A61B 8/465; A61B 8/565; A61B 8/5269; A61B 8/54
See application file for complete search history.

(56) References Cited

U.S. PATENT DOCUMENTS

| 4,998,132 A | 3/1991 | Kurogane |
| 5,617,371 A | 4/1997 | Williams |
| 5,903,516 A | 5/1999 | Greenleaf et al. |

(Continued)

FOREIGN PATENT DOCUMENTS

| AU | 2018250516 | 11/2018 |
| EP | 2 288 284 | 5/2016 |

(Continued)

OTHER PUBLICATIONS

Bradley, "Retrospective Transmit Beamformation", Whitepaper ACUSON SC2000™ Volume Imaging Ultrasounds System, Aug. 2008.

(Continued)

*Primary Examiner* — Chao Sheng
*Assistant Examiner* — Kaitlyn E Sebastian
(74) *Attorney, Agent, or Firm* — Knobbe, Martens, Olson & Bear, LLP

(57) ABSTRACT

Systems and methods for controlling contrast and time gain compensation (TGC) with a unified control. A system can include a first non-transitory computer storage medium for storing an ultrasound image, a second non-transitory computer storage medium for storing computer-executable instructions, and a computer hardware configured to execute the computer-executable instructions to at least cause presentation of the ultrasound image on a user interface of a display device using an initial contrast value for the ultrasound image and an initial time gain compensation value for at least two bands in the ultrasound image, each band being a portion of the displayed ultrasound image corresponding to a range of distances from an ultrasound scanner that generated the ultrasound image, and generate and cause display of a unified contrast/TGC (UTGC) control bar on the user interface for adjusting contrast and TGC of the displayed ultrasound image.

18 Claims, 5 Drawing Sheets

(56) References Cited

U.S. PATENT DOCUMENTS

| | | |
|---|---|---|
| 5,908,389 A | 6/1999 | Roundhill et al. |
| 6,031,529 A | 2/2000 | Migos |
| 6,063,030 A | 5/2000 | Vara et al. |
| 6,120,450 A | 9/2000 | Li |
| 6,123,670 A | 9/2000 | Mo |
| 6,132,374 A | 10/2000 | Hossack et al. |
| 6,400,981 B1 | 6/2002 | Govari |
| 6,607,489 B2 | 8/2003 | Hoctor |
| 6,690,963 B2 | 2/2004 | Ben Haim et al. |
| 6,908,434 B1 | 6/2005 | Jenkins et al. |
| 7,090,639 B2 | 8/2006 | Govari |
| 7,423,578 B1 | 9/2008 | Tietjen |
| 7,604,601 B2 | 10/2009 | Altmann et al. |
| 7,648,462 B2 | 1/2010 | Jenkins et al. |
| 7,667,639 B2 | 2/2010 | Cheng et al. |
| 7,682,358 B2 | 3/2010 | Gullickson et al. |
| 7,750,849 B2 | 7/2010 | Hjelmstad |
| 7,831,076 B2 | 11/2010 | Altmann et al. |
| 7,860,553 B2 | 12/2010 | Govari et al. |
| 7,918,793 B2 | 4/2011 | Altmann et al. |
| 7,996,060 B2 | 8/2011 | Trofimov et al. |
| 8,075,486 B2 | 12/2011 | Tal |
| 8,285,364 B2 | 10/2012 | Barbagli et al. |
| 8,390,438 B2 | 3/2013 | Olson et al. |
| 8,449,467 B2 | 5/2013 | Wilser et al. |
| 8,517,946 B2 | 8/2013 | Kim |
| 8,676,290 B2 | 3/2014 | Tegg |
| 8,690,871 B2 | 4/2014 | Partlett et al. |
| 8,702,612 B2 | 4/2014 | Hendriks et al. |
| 8,989,842 B2 | 3/2015 | Li et al. |
| 9,030,354 B2 | 5/2015 | Natarajan |
| 9,055,883 B2 | 6/2015 | Tgavalekos et al. |
| 9,095,682 B2 | 8/2015 | Romoscanu |
| 9,132,913 B1 | 9/2015 | Shapiro et al. |
| 9,179,890 B2 | 11/2015 | Ionasec et al. |
| 9,211,160 B2 | 12/2015 | Pivotto et al. |
| 9,261,595 B2 | 2/2016 | Garbin et al. |
| 9,323,445 B2 | 4/2016 | Kritt et al. |
| 9,342,156 B2 | 5/2016 | Huh |
| 9,922,554 B2 | 3/2018 | Mikuni et al. |
| 9,931,487 B2 | 4/2018 | Quinn et al. |
| 9,986,969 B2 | 6/2018 | Call et al. |
| 10,183,149 B2 | 1/2019 | Tegg et al. |
| 10,206,652 B2 | 2/2019 | Deno et al. |
| 10,368,951 B2 | 8/2019 | Moll et al. |
| 10,401,492 B2 | 9/2019 | Brooks |
| 10,405,830 B2 | 9/2019 | Garbin et al. |
| 10,463,439 B2 | 11/2019 | Joseph et al. |
| 10,499,882 B2 | 12/2019 | Hunter et al. |
| 10,537,307 B2 | 1/2020 | Yang |
| 10,555,780 B2 | 2/2020 | Tanner et al. |
| 10,624,612 B2 | 4/2020 | Sumi |
| 11,344,281 B2 | 5/2022 | Morisse et al. |
| 11,547,386 B1 | 1/2023 | Roy et al. |
| 2002/0173721 A1 | 11/2002 | Grunwald |
| 2002/0173722 A1 | 11/2002 | Hoctor et al. |
| 2003/0007598 A1 | 1/2003 | Wang et al. |
| 2003/0055334 A1 | 3/2003 | Steinbacher et al. |
| 2003/0055337 A1 | 3/2003 | Lin |
| 2004/0102700 A1 | 5/2004 | Asafusa |
| 2005/0288588 A1 | 12/2005 | Weber et al. |
| 2007/0027733 A1 | 2/2007 | Balle |
| 2007/0174772 A1 | 7/2007 | Gorman |
| 2007/0200760 A1 | 8/2007 | Hjelmstad |
| 2007/0239001 A1 | 10/2007 | Mehl et al. |
| 2007/0259158 A1 | 11/2007 | Friedman et al. |
| 2008/0012753 A1 | 1/2008 | Cheng |
| 2008/0114239 A1 | 5/2008 | Randall et al. |
| 2008/0215046 A1 | 9/2008 | Messing et al. |
| 2008/0306385 A1 | 12/2008 | Jago |
| 2009/0043206 A1 | 2/2009 | Towfiq et al. |
| 2009/0118620 A1 | 5/2009 | Tgavalekos et al. |
| 2009/0271704 A1 | 10/2009 | Cohen |
| 2010/0030076 A1 | 2/2010 | Vortman et al. |
| 2010/0081938 A1 | 4/2010 | Kato |
| 2010/0146431 A1 | 6/2010 | Raji et al. |
| 2010/0160784 A1 | 6/2010 | Poland |
| 2010/0168580 A1 | 7/2010 | Thiele |
| 2010/0251823 A1 | 10/2010 | Adachi |
| 2011/0077524 A1 | 3/2011 | Oshiki et al. |
| 2011/0137132 A1 | 6/2011 | Gustafson |
| 2011/0208052 A1 | 8/2011 | Entrekin |
| 2012/0075208 A1 | 3/2012 | Tamiya et al. |
| 2012/0157851 A1 | 6/2012 | Zwirn |
| 2012/0254747 A1 | 10/2012 | Bocirnea |
| 2013/0227052 A1 | 8/2013 | Wenzel |
| 2013/0234891 A1 | 9/2013 | Natarajan et al. |
| 2013/0238990 A1 | 9/2013 | Ubillos et al. |
| 2013/0253317 A1 | 9/2013 | Gauthier |
| 2013/0274712 A1 | 10/2013 | Schecter et al. |
| 2014/0035916 A1 | 2/2014 | Murphy |
| 2014/0046188 A1 | 2/2014 | Yen et al. |
| 2014/0058266 A1 | 2/2014 | Call et al. |
| 2014/0087342 A1 | 3/2014 | Campanatti, Jr. |
| 2014/0164965 A1 | 6/2014 | Lee et al. |
| 2014/0189560 A1 | 7/2014 | Caspi |
| 2014/0219059 A1 | 8/2014 | Younghouse |
| 2015/0019488 A1 | 1/2015 | Higginson et al. |
| 2015/0065877 A1 | 3/2015 | Orderud |
| 2015/0082251 A1 | 3/2015 | Lam |
| 2015/0293223 A1 | 10/2015 | Park et al. |
| 2016/0054901 A1 | 2/2016 | Yang et al. |
| 2016/0157824 A1* | 6/2016 | Park ................. A61B 8/463 |
| | | 600/437 |
| 2016/0161589 A1 | 6/2016 | Benattar |
| 2016/0161594 A1 | 6/2016 | Benattar |
| 2016/0161595 A1 | 6/2016 | Benattar |
| 2016/0165338 A1 | 6/2016 | Benattar |
| 2016/0165341 A1 | 6/2016 | Benattar |
| 2016/0338676 A1* | 11/2016 | Berger ................. G16H 20/40 |
| 2017/0090571 A1 | 3/2017 | Bjaerum |
| 2017/0153801 A1* | 6/2017 | Kim ..................... G06F 40/14 |
| 2017/0307755 A1 | 10/2017 | Brooks |
| 2017/0343655 A1 | 11/2017 | Solek et al. |
| 2017/0343668 A1 | 11/2017 | Brooks et al. |
| 2018/0000449 A1 | 1/2018 | Moore et al. |
| 2018/0000453 A1* | 1/2018 | Hunter ............. G06F 3/04883 |
| 2018/0055483 A1 | 3/2018 | Hunter |
| 2018/0064415 A1 | 3/2018 | Zhai et al. |
| 2018/0361145 A1 | 12/2018 | Mahapatra et al. |
| 2019/0245310 A1 | 8/2019 | Medina et al. |
| 2019/0261953 A1 | 8/2019 | Honjo et al. |
| 2019/0307427 A1 | 10/2019 | Levy et al. |
| 2019/0324139 A1 | 10/2019 | Brooks |
| 2019/0353975 A1 | 11/2019 | DiDomenico |
| 2020/0046321 A1 | 2/2020 | Duda |
| 2020/0060646 A1 | 2/2020 | Lindenroth et al. |
| 2020/0170662 A1 | 6/2020 | Vardi |
| 2020/0178928 A1* | 6/2020 | Park ....................... A61B 8/14 |
| 2020/0183004 A1 | 6/2020 | Gong et al. |
| 2020/0205783 A1 | 7/2020 | Shiran |
| 2020/0268351 A1 | 8/2020 | Chiang |
| 2020/0281565 A1 | 9/2020 | Yee et al. |
| 2020/0315592 A1 | 10/2020 | Soleimani et al. |
| 2021/0007710 A1 | 1/2021 | Douglas |
| 2021/0038334 A1 | 2/2021 | Hsu et al. |
| 2021/0125503 A1 | 4/2021 | Henry et al. |
| 2021/0177379 A1 | 6/2021 | Kolen et al. |
| 2021/0338208 A1 | 11/2021 | Nguyen et al. |
| 2021/0401508 A1 | 12/2021 | Zhao |
| 2022/0061811 A1 | 3/2022 | Eski |
| 2022/0061814 A1 | 3/2022 | Morrise |
| 2022/0156094 A1 | 5/2022 | Morrise |
| 2023/0059122 A1 | 2/2023 | Pellegrino |

FOREIGN PATENT DOCUMENTS

| | | |
|---|---|---|
| EP | 3 275 478 | 1/2018 |
| EP | 2 707 076 | 11/2018 |
| EP | 3 050 214 | 3/2019 |
| EP | 2 632 318 | 11/2019 |
| EP | 3 518 777 | 3/2021 |

(56) References Cited

FOREIGN PATENT DOCUMENTS

| WO | WO 12/088535 | 6/2012 |
| WO | WO 20/049012 | 3/2020 |
| WO | WO 20/252416 | 12/2020 |

OTHER PUBLICATIONS

Lin et al., Jun. 2010, A motion compounding technique for speckle reduction in ultrasound images, Journal of digital imaging 23(3):246-257.

* cited by examiner

ULTRASOUND UNIFIED CONTRAST AND TIME GAIN COMPENSATION CONTROL

BACKGROUND OF THE INVENTION

Field

This disclosure relates to contrast and controlling time gain compensation (TGC) for a displayed ultrasound image. Specifically, this disclosure relates to a unified control on a user interface for controlling contrast in the displayed image, and for controlling TGC separately in each of a number of bands of the displayed image.

Description of the Related Art

Ultrasound imaging is used in the diagnosis, screening, and treatment of a variety of diseases and conditions. An ultrasound image is created by transmitting sound waves into the body and then interpreting the intensity of the reflected echoes. The echoes are commonly used to produce two dimensional, three-dimensional, and color flow images of internal anatomical features of patients. The collected ultrasound images are collected and at least are initially analyzed in real-time during an examination such that being able to identify and understand the objects of interest in the ultrasound images is important for determining a condition of a patient.

To better identify objects in an ultrasound image, the display of the image may be adjusted using multiple controls on a user interface, for example, contrast and time gain compensation. The ultrasound images displayed may be adjusted while the ultrasound images are generated by an ultrasound imaging device which is held in one hand of the medical practitioner. It would be advantageous to be able to be able to efficiently and easily, adjust the contrast and the time gain compensation of a displayed ultrasound image using one hand. Also, is would be advantageous to be able to quickly, and separately, adjust contrast and time gain compensation to more easily identify objects in the ultrasound images as an ultrasound examination is being conducted.

SUMMARY

Provided herein is a system and method for controlling contrast and time gain compensation (TGC) for an ultrasound image, displayed in a user interface, using a unified contrast and time gain compensation (UTGC) control bar on the user interface. One innovation includes a system comprising a first non-transitory computer storage medium configured to store an ultrasound image, a second non-transitory computer storage medium configured to at least store computer-executable instructions, and one or more computer hardware processors in communication with the second non-transitory computer storage medium, the one or more computer hardware processors configured to execute the computer-executable instructions to at least: cause presentation of the ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image, and generate and cause display of a unified-contrast/TGC (UTGC) control bar on the user interface for adjusting contrast and TGC of the displayed ultrasound image.

Various embodiments of the such systems may include one or more other features, or different features. For example, the UTGC control bar can be configured to accept a user selection at a point on the control bar, the point corresponding to one of the bands, activate a contrast adjustment mode to increase the contrast of the displayed ultrasound image when the selected point is dragged in a first direction along the unified contrast/TGC control bar, and decrease the contrast when the selected point is dragged in a second direction along the unified-contrast/TGC control bar, the second direction opposite the first direction, and activate a TGC adjustment mode to increase the TGC of the displayed ultrasound image in the band of the displayed ultrasound image corresponding to the selected point when the selected point is dragged in a third direction, and decrease the TGC of the displayed ultrasound image in the band corresponding to the selected point to a second value when the selected point is dragged in a fourth direction that is opposite the third direction. The third direction can be substantially orthogonal to the first direction, and the fourth direction can be substantially orthogonal to the first direction. In some embodiments, the one or more computer hardware processors are further configured to execute the computer-executable instructions to store contrast and TGC information for the ultrasound image after the contrast and TGC have been adjusted such that the contrast and TGC information can be subsequently used for displaying the ultrasound image. In some embodiments, on the UTGC control bar, dragging the user selection in the first and second direction starting from any band adjusts contrast of all the bands. In some embodiments, the one or more computer hardware processors are further configured to execute the computer-executable instructions to present on the user interface the unified contrast/TGC control bar in a hidden-mode that is not visible on the user interface, and present on the user interface the unified contrast/TGC control bar in a visible mode in response to a pointing device selection on the display at a location corresponding to the hidden unified contrast/TGC control bar. In some embodiments, the unified contrast/TGC control bar is presented on the user interface in the hidden-mode on the right edge of the user interface. In some embodiments, the right edge of the user interface corresponds to a portion of the user interface within 25% of the right side of the user interface. In some embodiments, the unified contrast/TGC control bar is presented in the hidden-mode on the left edge of the user interface. In some embodiments, the left edge of the user interface corresponds to a portion of the user interface within 25% of the left side of the user interface.

Other embodiments of such systems can include other features. For example, in some embodiments, the one or more computer hardware processors are further configured to execute the computer-executable instructions to hide the unified contrast/TGC control bar during ultrasound scanning. In some embodiments, the unified contrast/TGC control bar contains boxes (e.g., grayscale boxes) which correspond to the TGC bands of the image, wherein the shade of the box represents the effect of both contrast and TGC on the portion of the image in a band. These 'boxes' may be referred to as UTGC boxes herein. In some embodiments, the one or more computer hardware processors are further configured to execute the computer-executable instructions such that UTGC boxes are zoom and pan sensitive, that is they align correctly when the image is zoomed or panned. In some embodiments, the one or more computer hardware processors are further configured to execute the computer-executable instructions to adjust all of the bands simultaneously. In some embodiments, the one or more computer hardware processors are further configured to execute the computer-executable instructions to generate and present on the user interface a contrast icon that indicates a digital value of the contrast. In some embodiments, the one or more computer hardware processors are further configured to execute the computer-executable instructions such that once the contrast adjustment mode is activated it continues even if the user drags the selected point in the third or fourth direction to adjust the TGC. In some embodiments, the one or more computer hardware processors are further configured to execute the computer-executable instructions such that once the contrast adjustment mode is activated it continues even if the user drags the selected point in the third or fourth direction to adjust the TGC. In some embodiments, the one or more computer hardware processors are further configured to execute the computer-executable instructions to reset the contrast to a default value by double-tapping the contrast icon. In some embodiments, the third direction is left and the fourth direction is right, relative to the user interface. In some embodiments, the third direction is right and the fourth direction is left, relative to the user interface. In some embodiments, the unified contrast/TGC bar includes a box that corresponds to each band, and dragging left and right in a box that corresponds to the selected point adjusts TGC for the band corresponding to the box. In some embodiments, the one or more computer hardware processors are further configured to execute the computer-executable instructions to adjust the TGC only for the band corresponding to the box of the selected point. In some embodiments, the one or more computer hardware processors are further configured to execute the computer-executable instructions such that if the user selected point is dragged to a second box, the TGC corresponding to the second box will be adjusted.

In some embodiments, the one or more computer hardware processors are further configured to execute the computer-executable instructions to generate and display horizontal grid lines for all TGC bands when adjusting the TGC for any of the bands. In some embodiments, the one or more computer hardware processors are further configured to execute the computer-executable instructions to generate and display a TGC a numerical value for the adjustment on the box for each band when the TGC is adjusted. In some embodiments, the one or more computer hardware processors are further configured to execute the computer-executable instructions to reset each TGC band to a default value by double-tapping a control icon displayed on the user interface. In some embodiments, the one or more computer hardware processors are further configured to execute the computer-executable instructions such that once the user stops dragging by unclicking or untouching, the UTGC control bar remains displayed for a duration of five seconds or less and then disappears. In some embodiments, the one or more computer hardware processors are further configured to execute the computer-executable instructions to enter a contrast mode or a TGC mode immediately after when touching the UTGC control bar (or area) without waiting for the UTGC control bar to appear. In some embodiments, the one or more computer hardware processors are further configured to execute the computer-executable instructions to animate both the appearance and disappearance of the UTGC control bar. In some embodiments, the one or more computer hardware processors are further configured to execute the computer-executable instructions to control the number and spacing of the TGC bands by receiving an input through the user interface of a number of bands or of a band spacing.

Another innovation includes a method of controlling contrast and time gain compensation using a unified control. In some embodiments of such methods, presenting the ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image; and generating and displaying a unified-contrast/TGC (UTGC) control bar on the user interface for adjusting contrast and TGC of the displayed ultrasound image. Embodiments of such methods can include additional features. For example, the method can further include accepting a user selection at a point on the control bar, the point corresponding to one of the bands, activating a contrast adjustment mode to increase the contrast of the displayed ultrasound image when the selected point is dragged in a first direction along the unified contrast/TGC control bar, and decrease the contrast when the selected point is dragged in a second direction along the unified-contrast/TGC control bar, the second direction opposite the first direction, and activating a TGC adjustment mode to increase the TGC of the displayed ultrasound image in the band of the displayed ultrasound image corresponding to the selected point when the selected point is dragged in a third direction, and decrease the TGC of the displayed ultrasound image in the band corresponding to the selected point to a second value when the selected point is dragged in a fourth direction that is opposite the third direction. The third direction can be substantially orthogonal to the first direction, and the fourth direction can be substantially orthogonal to the first direction. The method can further include storing contrast and TGC information for the ultrasound image after the contrast and TGC have been adjusted such that the contrast and TGC information can be subsequently used for displaying the ultrasound image. In some embodiments, the method can further include dragging the user input (or selection) in the first and second direction starting from any band to adjust contrast of the entire image (e.g., the image displayed in all the bands). In some embodiments, to perform this process the user interface is configured to receive a user input (e.g., using a user input device such as a mouse, joystick, or a user touch on a touchscreen of a display displaying the user interface) and based on which direction the user input is moved, the contrast is increased or decreased. The method can also include presenting the unified contrast/TGC control bar in a hidden-mode that is not visible on the display, and display the unified contrast/TGC control bar in response to a pointing device selection on the display at a location corresponding to the hidden unified contrast/TGC control bar. The method can also include presenting the unified contrast/TGC control bar in the hidden-mode on the right edge of the user interface. In some embodiments, the right edge of the user interface corresponds to a portion of the user interface within 25% of the right side of the user interface. The method can also include presenting the unified contrast/TGC control bar in the hidden-mode on the left edge of the user interface. In some embodiments, the left edge of the user interface corresponds to a portion of the user interface within 25% of the left side of the user interface. In some embodiments, the method can further include hiding the unified contrast/TGC control bar during ultrasound scanning.

In some embodiments of controlling contrast and time gain compensation using a unified control, the unified contrast/TGC control bar contains grayscale boxes which correspond to the TGC bands of the image, wherein the shade of the box represents the effect of both contrast and TGC on the portion of the image in a band. In some embodiments, the UTGC boxes are zoom and pan sensitive, and they align correctly when the image is zoomed or panned. In some embodiments, the method further comprises adjusting all of the bands simultaneously. In some embodiments, the method further comprises generating and presenting on the user interface a contrast icon that indicates a digital value of the contrast. In some embodiments, once the contrast adjustment mode is activated it continues even if the user drags the selected point in the third or fourth direction to adjust the TGC. In some embodiments, once the contrast adjustment mode is activated it continues even if the user drags the selected point in the third or fourth direction to adjust the TGC. In some embodiments, the method further comprises resetting the contrast to a default value by double-tapping the contrast icon. In some embodiments, the third direction is left and the fourth direction is right, relative to the user interface. In some embodiments, the third direction is right and the fourth direction is left, relative to the user interface. In some embodiments, the unified contrast/TGC bar includes a box that corresponds to each band, and dragging left and right in a box that corresponds to the selected point adjusts TGC for the band corresponding to the box. In some embodiments, the method adjusts the TGC only for the band corresponding to the box of the selected point. In some embodiments, the control bar operates such that if the user selected point is dragged to a second box, the TGC corresponding to the second box will be adjusted. In some embodiments, the method further comprises generating and displaying horizontal grid lines for all TGC bands when adjusting the TGC for any of the bands. In some embodiments, the method further comprises generating and displaying a TGC a numerical value for the adjustment on the box for each band when the TGC is adjusted. In some embodiments, the method further comprises resetting each TGC band to a default value by double-tapping a control icon displayed on the user interface. A method can further include displaying the UTGC control bar for a duration of five seconds or less and once the user stops interacting with the UTGC control bar by unlicking or un-touching the UTGC control bar. A method can further include entering a contrast mode or a TGC mode immediately after touching the UTGC control bar (e.g., the area on the display relating to the control bar) without waiting for the UTGC control bar to appear. A method can further include animating both the appearance and disappearance of the UTGC control bar. A method can further include receiving a band number input through the user interface and setting the number of bands on the displayed imaged based on the band number input. A method can further include receiving a band spacing input through the user interface and setting the band spacing based on the received input.

BRIEF DESCRIPTION OF THE DRAWINGS

FIG. 3 also illustrates that the UTGC control bar and the ultrasound image is displayed in a plurality of bands, in this example five bands.

DETAILED DESCRIPTION OF CERTAIN INVENTIVE ASPECTS

Overview

Figure 1:
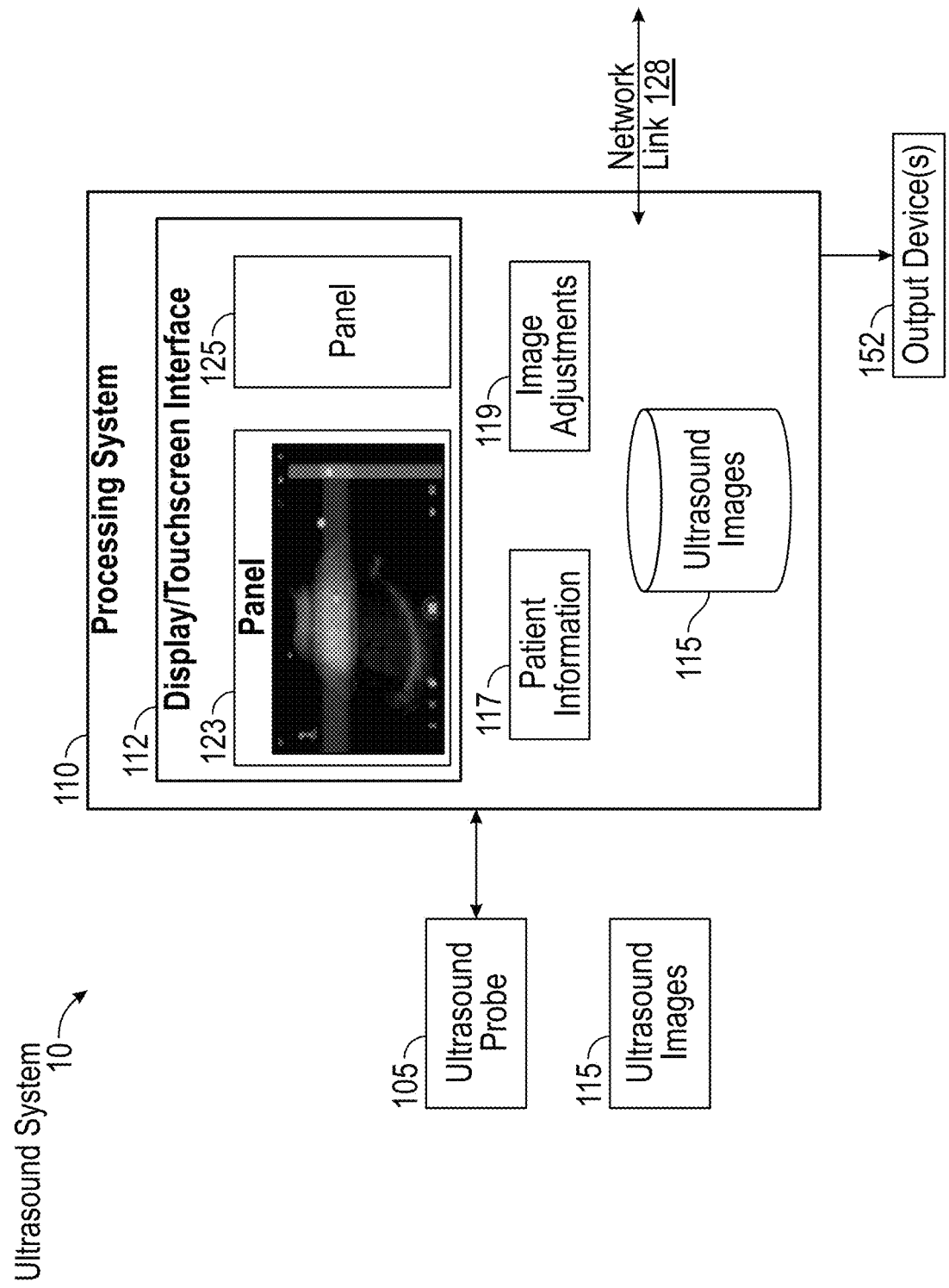
FIG. 1 is a block diagram illustrating an example of an ultrasound system that can generate and display a user interface that includes a unified contrast and time gain compensation control.

Embodiments of systems and methods for providing a unified contrast and time gain compensation are disclosed herein. A software application provides a user interface for displaying and interacting with ultrasound images. The interactions may include adjusting image display parameters for a user to better visually analyze objects in the displayed image. The interactions may also include identification, annotation, and measurement of objects in an ultrasound image, including suspect objects and a patient's anatomy in an image. For example, a method for controlling contrast and time gain compensation using a unified control, may include causing presentation of the ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image, and generating and displaying a unified-contrast/TGC (UTGC) control bar on the user interface for adjusting contrast and TGC of the displayed ultrasound image. The method may also include accepting a user selection at a point on the control bar. For example, by selecting on the control bar at a certain point that corresponds to a "band" where each band corresponds to a portion of the displayed image at a range of "depths" (e.g., a range of distances from the ultrasound probe imaging array). In some embodiments, the user interface is a touchscreen. A point is selected by the user touching the screen, with the user's finger, at the selected point and then dragging the point to adjust contrast (e.g., of the entire image) and/or dragging the point to adjust the TGC within a band. For example, in the band in the image in which the user touches. In some embodiments, the user selects the point of the control bar with a pointing device (e.g., mouse, trackball, etc.). In some embodiments, the user touches (or "clicks") and then drags the selection up, down, left, or right (relative to the orientation of the user interface) to adjust the contrast and TGC. The contrast adjustment increases the contrast of a displayed ultrasound image when the selected point is dragged in a first direction along the UTGC control bar, and decreases the contrast when the selected point is dragged in a second direction on the UTGC control bar, the second direction opposite the first direction.

The TGC of the band is increased when the point is dragged in a third direction, and the TGC is decreased when the point is dragged in a fourth direction that is opposite the third direction.

Using the described unified UTGC control bar, both the contrast of the entire image and the TGC of a particular band (in which the selection or touch is made) can be adjusted quickly, easily, and in one touch and drag operation moving the selected point up/down and left/right. An ultrasound image can be displayed in a band format with band gridlines presented on the user interface. The number of bands and the width (or spacing) of the bands can be adjusted via the user interface. The UTGC control bar can be displayed on the left or right side of the user interface, e.g., on either side of a displayed ultrasound image.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

"Database" in this context refers to an organized collection of data (states of matter representing values, symbols, or control signals to device logic), structured typically into tables that comprise 'rows' and 'columns.'

"Final Report" in this context refers to the final product of an ultrasound scan including written documentation of the imaging findings and an impression or diagnosis based on those findings.

"Graphical representation" in this context refers to a stylized drawing of the body part being scanned.

A "loop", "cineloop", "time-lapse", or "video loop" in this context may be used interchangeably to refer to a time series of images. In some embodiments, a 4D image may be a time-lapse of 3D image(s). In other embodiments, individual frames can be sequenced to form a video loop.

"Module" in this context refers to logic having boundaries defined by function or subroutine calls, branch points, application program interfaces, or other technologies that provide for the partitioning or modularization of particular processing or control functions. Modules are typically combined via their interfaces with other modules to carry out a machine process.

"Protocol" in this context refers to a written outline, checklist, or worksheet that list images and measurements that should be acquired during the specified ultrasound examination.

"Reader" in this context refers to the person interpreting the ultrasound scan.

A "scanner" or "ultrasound device" in this context refers to a device for performing ultrasound imaging (sonography), which uses high-frequency sound waves to examine an object. The device may comprise an ultrasonic transducer or an ultrasonic transducer array used to probe the object. Transducers may be part of a sequential array in which the acoustic beam is focused straight in front of the transducer, providing high sensitivity but a limited field of view, or a phased array in which each transducer sends an acoustic beam in a coordinated sequence, establishing a pattern of constructive interference that results in a beam at a set angle, allowing for a wider field of view. Phased array transducers may comprise multiple transducer elements which may be arranged in a variety of shapes including a strip (linear array), a ring (annular array), a circular matrix (circular array), conformal array, curved, or a more complex shape. A "scanner" used herein may be hand-held or portable.

"Ultrasound study" in this context refers to a diagnostic procedure performed by a sonographer that uses two-dimensional images produced by inaudible sound waves to evaluate an anatomical feature.

"User" in this context refers to the person performing an ultrasound scan. "Reader" in this context refers to the person interpreting an ultrasound scan. A "sonographer" may both perform and interpret an ultrasound scan.

"Scan plane" in this context refers to the orientation of the ultrasound probe relative to the part being scanned.

When 3D imaging is available, ultrasound viewing and saving may include three modes: scanning, frozen, and review. "Scanning" in this context refers to showing images directly from the scanner (e.g., the ultrasound device). "Frozen" in this context refers to showing the last N seconds of images from the scanner. "Review" in this context refers to showing images that are explicitly saved.

A "frame" in this context is for specifying the space and time aspect of an image. In other words, a frame is the image at a given position with respect to the time the image was taken. In some embodiments, a "frame" may be a 2D image. In other embodiments, when a user is performing the 3D imaging mode via an ultrasound device, a "frame" may additionally cover each image taken by the ultrasound device in that same instance.

"Scan plane" in this context refers to the orientation of the ultrasound probe relative to the part being scanned.

"Structured labels" in this context refers to a list of labels used for a specific exam type in which the labels are automatically presented in a set order.

"Slices": Bundled images in frozen and review modes are called a "capture" and there are four types of capture: 2D image, 2D series (cineloop), 3D image, and 3D series (3D cineloop). The information (or image data) that constitute ultrasound 3D image captures are called "slices". A "slice" in this context may be a thin 3D composite image formed from a collection of 2D images.

A "thick slice mode" in this context refers to a 3D image taken by an ultrasonic transducer array. A "tomography" in this context refers to a time series of 2D or 3D images taken by an ultrasonic transducer array is in motion relative to the object being scanned.

"Touch screen" in this context refers to a capacitive or resistive display which responds to direct touch manipulation, either by finger (simple or multi-touch), stylus, or both. The user can use the touch-screen to react to what is displayed and to control how it is displayed. The touch-screen enables the user to interact directly with information displayed rather than using a mouse, touchpad, or other intermediate device (with the exception of a stylus).

"Ultrasound study" in this context refers to a diagnostic procedure performed by a sonographer that uses two-dimensional images produced by inaudible sound waves to evaluate an anatomical feature.

"User" in this context refers to the person actually performing the ultrasound scan.

"Visual Protocol" in this context refers to a protocol that is displayed on a display screen of a computer system, and that is updated based on a user's interactions. The visual protocol can associate a protocol checklist with a diagram of a scan map (a diagram of the scanned body part). The visual protocol can also associate the protocol checklist with a textual list of annotations for the image and a series of thumbnail images (a "gallery"), where each of the thumbnail images is associated with a full-size ultrasound image that can be when the thumbnail image is selected. The visual protocol can also associate the protocol checklist with measurements that are to be acquired during the specified ultrasound examination.

"Word bank" in this context refers to a list of context-specific labels which are commonly used for a specific scan type or body part.

"Worksheet" in this context refers to a generated softcopy or hardcopy document that can include patient information, scan information, images, and/or written findings related to an ultrasound examination or procedure.

Data Representation

In some embodiments, the data representation of a scanned image may be able to represent all the needed fields to both display and to signify the exact display variant the renderer should use. Additionally, the data format may be flexible enough to allow for transformations to other supported display variants if possible.

The data implementation may represent a single slice or a single frame, or captures which are collections of images along with other properties. Checking the contents of captures allows for explicitly knowing the type of scan and variant needed to display. Knowing this type then specifies all actions that can be taken on the capture, as well as directing the display renderer how it should render the image data.

An image may be a single frame or a single slice. In some embodiments, image data that is saved to the database for an individual image may include the following immutable fields:
(1) Raw pixel data for what was imaged.
(2) Depth details to specify constraint of bottom of image. The depth refers to a 2D image's y-axis which corresponds to how deep the scanner is imaging.
(3) Timestamp to have relative timing information relative to other image data
(4) Relative position data in x, y, and z directions.
(5) Relative angle position data in x, y, and z directions.
(6) Relative slice position and total number of slices for beamformed 3D image if applicable.

Bundled images in frozen and review modes are called a capture. A capture may be a 2D image, a 2D series (cineloop), a 3D image, or a 3D series (3D cineloop). A capture may include multiple frames and/or slices, where the multiple frames may include images that are changing in time, and multiple slices may include images that are changing spatially. A capture may be the full collection of the images taken over both time and space. Different capture types represent different display variants, including:
(1) A "frame", which is a single image at a given time point.
(2) A "loop", which include multiple images focused on essentially the same spatial area but changing in time.
(3) A "slice", which includes images of a spatial range near a spatial position. Multiple slices are used to create a 3D image.
(4) A "2D time-lapse" or a 3D "time-lapse", which includes images taken in the same location over a time range.
(5) A "thick slice", which includes images taken in 3D mode in a stable location with a given spatial and time sampling rate.
(6) A "tomography", which includes images taken while traversing (moving the scanning probe) a region that is both time and spatially variant.
(7) A "loop", which is a time series of data. The spatial information can be rendered in 3D or as a 2D plane. As each image data has time and spatial information, projections between the different dimensions can be made.

Example Ultrasound System with Unified Contrast and TGC Control

FIG. 1 is a block diagram illustrating an example of an ultrasound system 10 that includes a unified contrast and TGC control. The ultrasound system 10 includes an ultrasound probe 105 that communicates with a processing system 110. The ultrasound probe 105 can be a handheld ultrasound device that comprises a transducer array configured to transmit an ultrasound signal to a target object, receive an ultrasound echo signal reflected from the target object, and form ultrasound data corresponding to the target object. The processing system 110 can be any type of computer device (e.g., a desktop computer, a tablet, a laptop, or another mobile device) that is suitably configured to perform visual protocols. The ultrasound probe 105 can be controlled by the processing system 110 to provide ultrasound images to the processing system 110. When the ultrasound system is being used to view stored ultrasound images, the processing system 110 can operate as described herein without input from the ultrasound probe 105.

The processing system 110 can include a display/touchscreen interface 112 ("interface") that can display a ultrasound images, image display information, measurement information, and other information related to a ultrasound imaging in one or more panels 123, 125, etc. In some preferred embodiments, the display screen and the interface 112 are implemented together such that most, or all, of the controls are available on the interface 112. Some embodiments of systems, however, may have a separate display and user interface. The interface can be any type of a flat screen, LED screen, electroluminescent display, organic LED, LCD, virtual display and the like that can display information and receive input from a user in the directly to the display or to another device that is in communication with the display. The processing system 110 may also include voice recognition to manipulate information and/or images on the interface 112.

Still referring to FIG. 1, the interface 112 may present information in a variety of ways. In some embodiments, the interface 112 is divided into a plurality of panels (or sectors) 123, 125, etc. each of which may contain one or more of: patient information, an active ultrasound image being currently acquired from a machine transformation of an ultrasound reading in process (active scan), and image display controls. As described in more detail in reference to FIG. 2, the interface 112 can display information related to controlling the display of an ultrasound image, and receive user input via its touchscreen functionality, or other input devices (e.g., keyboard, mouse, and the like) that are in communication with the processing system 110.

In some embodiments, analyzing an ultrasound image may generally include, for example, controls for selecting an ultrasound procedure to perform, associating ultrasound images with a patient, and receiving ultrasound images from the ultrasound probe 105. Performing the visual protocol may also include recording, associating, measuring comparing, labeling, reporting and/or documenting information received from an ultrasound probe. The plurality of panels 123, 125 on the interface 112 allow for the display of the controls for interacting with one or more ultrasound images, graphical representations, and measurement of objects depicted in ultrasound images. The processing system 110 may include various modules to facilitate the completion of a procedure, for example, the processing system 10 may include a unified contrast and TGC control bar activated by the user interface.

The processing system 110 may store information that is used to perform the visual protocol. For example, the processing system 110 may store ultrasound images 115, patient information 117, and image adjustment information 119 (e.g., image processing information). Other information and data may also be stored (e.g., visual protocols, scan maps, etc.). In some embodiments, one or more of the ultrasound images 115, patient information 117, and image adjustment information 119 (e.g., image processing information) are stored on a system that is in communication with the processing system 110 via a network link 128. For example, because of the potentially large size of the images that may be collected while performing un ultrasound procedure at least some of the ultrasound images that are collected may be stored on a high-speed computer storage device is in communication with the processing system 110 via the network link 128. The processing system 110 may also include one or more output devices 152 that can be used to, for example, generate a report or provide information and images that are stored and subsequently used for further analysis of a patient.

As mentioned above, the interface 112 in FIG. 1 may be a combination display and touch screen that allows the user to manipulate the images on the display. Touch-screen based computers comprise computer assemblies combining an internal computer processor and touch sensitive digital display screen. The display and the computer's ability to monitor the positions and motions of finger touches on the touch-screen are coordinated such that finger contact locations can be correlated by the computer with the information displayed at those locations. A variety of gestures may be used to interact with the interface 112, including, but not limited to, touching, swiping, double tap, multiple finger taps, pinch, multi-touch, radio buttons and the like. A processor is coupled to the touch-screen for detecting a touch by the user on the touch-screen that identifies a selected activation area. The processor then performs the device function associated with the stored image manipulation function thereby activating the selected activation area. In some embodiments, the user may interact with the interface 112 through voice recognition, a stylus, keyboard, mouse, virtual reality headset, hand gestures in the air, any other way generally used to interact with a user interface, or a combination thereof. In some embodiments, controls on the ultrasound probe 105 may be used to input information onto either or both the interface 112.

The interface 112 can be divided into a plurality of control panels including, but not limited to, a proportionate graphical representation of the anatomical part being scanned, a scale or other measuring apparatus, a track pad, a series of one or more virtual controls such as buttons or radio buttons, word bank, structured label bank, tabbed drop down menus, virtual keyboard, active ultrasound image, virtual trackpad, virtual depth and focus sliders, virtual cine slider, and virtual time gain compensation sliders. In some embodiments, the number and arrangement of control panels may be altered to suit the needs of the user. For example, during a scan, it may be desirable to have an extended display of one or more of the control panels. In some embodiments, there may be one control panels. In other embodiments, there may be 2, 3, 4, 5, 6, 7, 8, 9, 10, or more control panels. Activation of each panel on the interface 112 may perform a function on interface 112 and can manipulate information on the interface 112.

Figure 2:
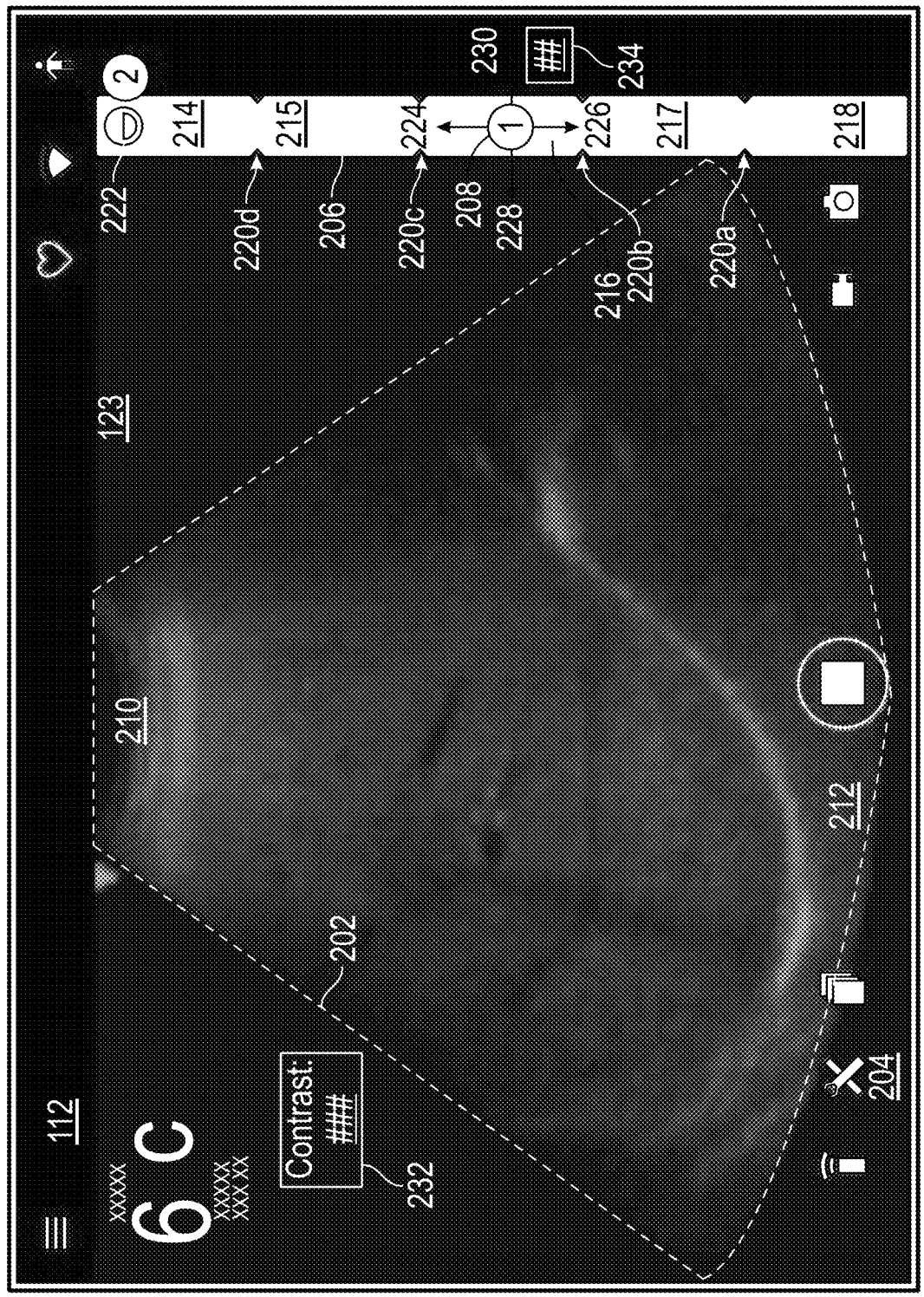
FIG. 2 is a picture of an example of a user interface that is generated and presented on a display, the user interface having unified contrast and time gain compensation control.

FIG. 2 illustrates an example of a user interface 112 that is generated and presented on a display of a processing system, for example, the processing system 110 illustrated in FIG. 1. The user interface 112 includes panel 123 that can be used to display an ultrasound image, and information and controls relating to the displayed ultrasound image. As shown in FIG. 2, in this example user interface 112 is displaying ultrasound image 202. In FIG. 2, the ultrasound image 202 is delineated by a dashed line for reference. A proximal portion 210 of the ultrasound image is displayed on an upper portion of the user interface 112 and a distal portion 212 of the ultrasound image is displayed on a lower portion of the user interface 112 (the "upper" and "lower" portions relative to the orientation of the FIG. 2). The proximal portion 210 is a portion of the ultrasound image 202 that was closer to the ultrasound probe 105 when the ultrasound image 202 was captured, and thus corresponds to information in the object being imaged (e.g., a human or animal body) that was closer to the ultrasound probe 105 and at a shallower "depth" in the object. The distal portion 212 of the ultrasound image 202 is a portion of the ultrasound image that was farther from the ultrasound probe 105 when the image was captured, and thus corresponds to information in the object being imaged that was farther from the ultrasound probe 105 and at a deeper "depth" in the object.

Various embodiments of the user interface 112 can have a unified contrast and time gain compensation control. In the example in FIG. 2, the user interface 112 includes a unified contrast and time gain compensation (UTGC) control bar 206. In this example, the user interface 112 is configured to display the UTGC control bar 206 vertically (with respect to the orientation of FIG. 2) along a right-hand portion of the user interface 112. In various examples, the UTGC control bar 206 can be displayed along the left-hand side of the user interface 112, or positioned closer to the right or left-hand side of the user interface 112. Preferably the UTGC control bar 206 is positioned at a location where it does not obscure the displayed ultrasound image 202, or only obscures a minimal amount of the image (e.g., less than 1%, 2%, 3%, 4%, 5%, 6%, 7%, 8%, 9%, or 10% of the ultrasound image). The user interface 112 may be configured to display the UTGC control bar 206 at all times, or only when the "hidden" UTGC control bar 206 is touched or scrolled over, e.g., by a touch input on a touchscreen or by a pointing device. In some embodiments, UTGC control bar 206 is displayed on the user interface 112 in a visible mode, or displayed on the user interface in a non-visible or "hidden" mode, based on an input from a button or selection of a menu item on the user interface. The size and/or the transparency of the UTGC control bar 206 may be set by a user using a control bar configuration window. The sensitivity of adjusting the contrast and adjusting the time gain compensation may also be adjusted using a control bar configuration window.

Portions of the UTGC control bar 206 correspond to a range of depths of the image. For example, an upper portion of the UTGC control bar 206 corresponds to the proximal portion 210, and a lower portion of the UTGC control bar 206 corresponds to the distal portion 212. The UTGC control bar 206 can be segmented into bands (or sections) 214, 215, 216, 217, 218 that correspond to bands across the image, each band corresponding to a range or depths of the image. In this example the UTGC control bar 206 and the image are divided into five bands each of a certain size or spacing. The number of bands and/or the spacing may be set by a user input, for example, in the pop-up control bar configuration window (now shown). The UTGC control bar 206 can be displayed to have band separation indicators 220 on one or both sides of the UTGC control bar 206 that indicate where a band starts and an adjacent band stops. In this example, the band separation indicators are shown as small indentations on both sides of the UTGC control bar 206. The User interface can have other controls 204 for analyzing the ultrasound image, for example, for measuring or analyzing an object depicted in an ultrasound image.

In operation, the user interface 112 displays an ultrasound image 202 from the ultrasound probe 105. The UTGC control bar 206 also can be displayed on the left or right-side of the use interface 112. To adjust the contrast of the displayed image, a user selects a point 208 on the UTGC control bar 206, for example, the point "1" as shown in FIG. 2. If the user interface 112 is displayed on a touchscreen, the point 208 can be selected by the user touching the UTGC control bar 206. In some embodiments, the point 208 can be selected by a pointing device (e.g., a mouse, trackball, touchpad, etc.).

In some embodiments, the UTGC control bar 206 is configured to adjust the time gain compensation (TGC) of the band associated with the selected point 208 when the selected point 208 is dragged. The user interface 112 can be configured to display a value indicative of the contrast of the displayed ultrasound image. In an example, the user interface 112 can be configured to display a field 232 that indicates the contrast of the displayed ultrasound image (e.g., the field displays a value indicative of the contrast of the displayed ultrasound image). In some examples, the position of the field 232 on the user interface 112 may vary based on the embodiment, or based on user preference. In some embodiments, the user interface 112 is configured to allow the user to selected the field 232 and drag the field 232 to a desired location on the user interface 112.

The user interface 112 can also be configured to display a value indicative of the TGC of a band of the ultrasound image, for example, the band associated with the selected point 208. In an example, the user interface 112 can be configured to display a field 234 that indicates the TGC of a band of the displayed ultrasound image in a (e.g., the field 234 displays a value indicative of the TGC of the displayed ultrasound image). In some embodiments, the user interface 112 can be configured to display a field 234 that indicates the TGC of each of the bands of the displayed ultrasound image. In some examples, the position of the field 234 on the user interface 112 may vary based on the embodiment, or based on user preference. In some embodiments, the user interface 112 is configured to allow the user to selected the field 234 and drag the field 234 to a desired location on the user interface 112.

In some embodiments, the time gain compensation of the band associated with the selected point 208 (e.g., adjacent to the selected point) can be increased dragging the selected point in one direction or decreased by dragging the selected point in another direction. In some embodiments, the UTGC control bar 206 is configured to adjust the contrast of the image (e.g., the entire image) when the selected point 208 is dragged. For example, the contrast of the image can be increased of the selected point 208 is dragged in a one direction, and decreased when dragged in another direction. In some embodiments, the UTGC control bar 206 is configured to adjust the time gain compensation of a band associated with the selected point 208 when the selected point 208 is dragged, and to adjust the contrast of the image when the selected point is dragged, as described further below.

The UTGC control bar 206 may be configured to increase or decrease the contrast of the entire image when the selected point 208 is dragged along the UTGC control bar 206 in different directions. In an example, the contrast of the image is increased when the point 208 is dragged in a first direction 224, and the contrast is decreased when the point 208 is dragged in a second direction 226. When contrast is adjusted, the user interface 112 can display a contrast icon 222 that indicates a contrast level that the image is adjusted to. In this example, the contrast icon 222 is displayed on the top of the UTGC control bar 206. In other examples, the contrast icon 222 can be displayed on the user interface 112 in a different location. Still referring to FIG. 2, the UTGC control bar 206 is also configured to adjust the time gain compensation of a band of the displayed image by dragging the selected point 208 laterally across the UTGC control bar 206. For example, in a third direction 228 to decrease the time gain compensation and in a fourth direction 230 to increase the time gain compensation. The time gain compensation adjustment is performed only in the band that corresponds to the selected point. For example, in FIG. 2 the selected point 208 corresponds to band 216 which extends horizontally across the displayed image 202 (in reference to the orientations shown in FIG. 2). When the selected point 208 is dragged to the right (fourth direction 230) the time gain compensation for band 216 is increased, and when the selected point 208 is dragged to the left (third direction 228) the time gain compensation for band 216 is decreased. Thus, the configuration of the UTGC control bar 206 allows the user to select a point corresponding to a particular band of interest (e.g., bands 214, 215, 216, 217, 218) and adjust the contrast of the entire image by dragging the selected point in the first direction 224 or the second direction 226, and simultaneously adjust the time gain compensation of the band that corresponds to the selected point by dragging the selected point in the third direction 228 or the fourth direction 230. To adjust time gain compensation in a different band, another point on the UTGC control bar 206 that corresponds to the band of the displayed image to be adjusted is selected and time gain compensation is adjusted by dragging the point in the third direction 228 (e.g., to the left) or in the fourth direction 230 (e.g., to the right). The configuration of the user interface 112 and the UTGC control bar 206 to allow the contrast and time gain compensation to be adjusted intuitively and simultaneously increases efficiency of these adjustments as are typically performed in real time during the examination. In particular, the configuration of the user interface 112 and the UTGC control bar 206 to adjust the contrast and time gain compensation with a single touch (or click) and drag allow such adjustments to be done quickly with a single touch and swipe. The configuration of the user interface such that the placement of the UTGC control bar 206 along the image 202 so portions of the UTGC control bar 206 correspond with horizontally adjacent portions of the image allows the user to intuitively select a portion of the image where they want to adjust the time gain compensation.

Figure 3:
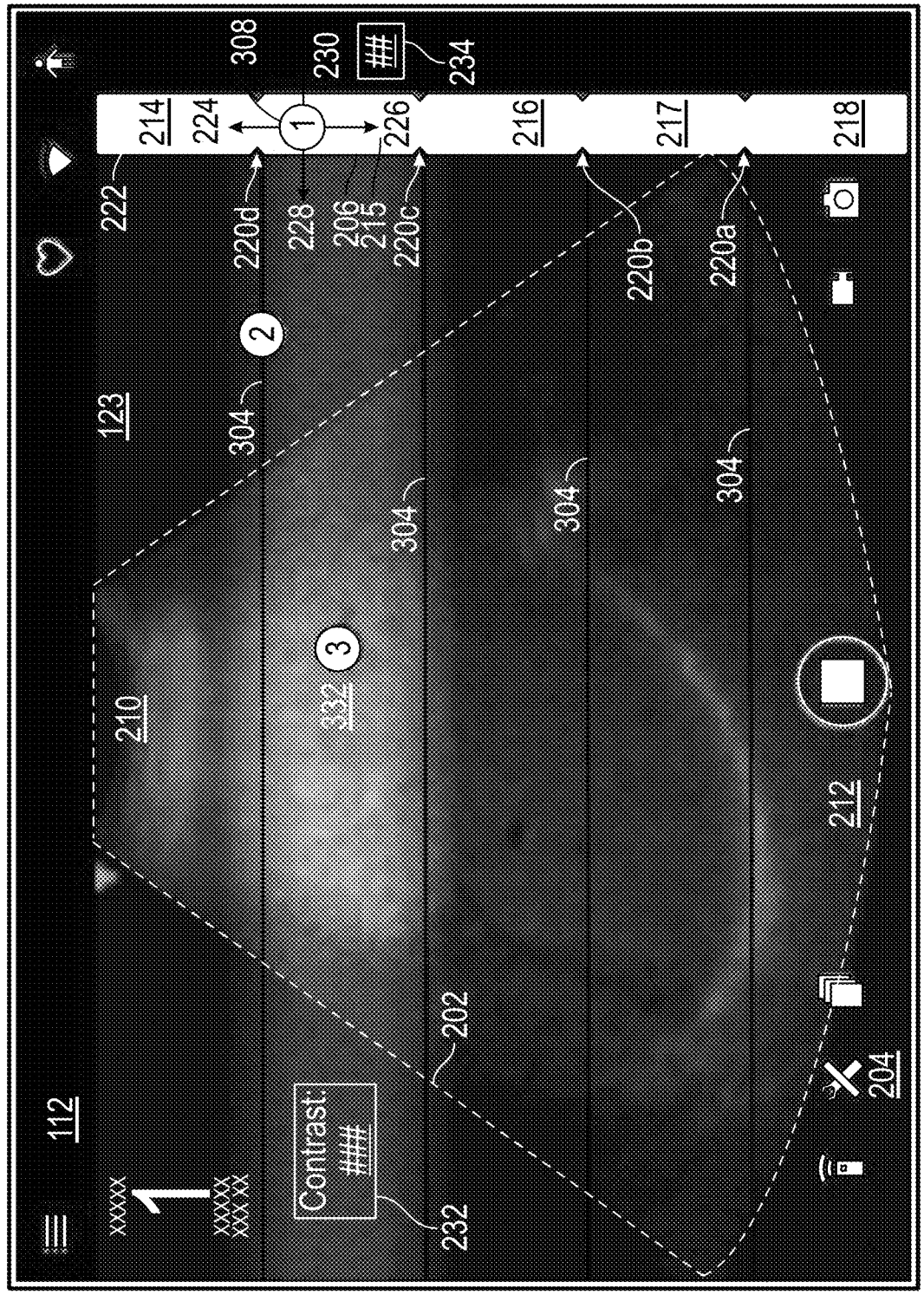
FIG. 3 is a picture of an example of the user interface illustrated in FIG. 3, now showing the ultrasound image, a unified contrast and time gain compensation (UTGC) control bar that is generated and presented on the right-hand side of the user interface. In this example, the UTGC control bar is displayed within about 25% of the right-hand side of the user interface, relative to the entire size of the user display.

FIG. 3 is a picture of another example of the user interface 112 illustrated in FIG. 2, showing the ultrasound image 202, the UTGC control bar 206 that is generated and presented on the right-hand side of the user interface. In this example, the UTGC control bar is displayed within about 25% of the right-hand side of the user interface, relative to the entire size of the user display. FIG. 3 also illustrates that the user interface 112 is configured to includes gridlines 304 that indicate the location of the bands on the image 202 and the UTGC control bar 206. The gridlines 304 can be optionally displayed based on a user input.

In FIG. 3, the selected point 308 corresponds to band 215. The gridlines 304 are shown extending laterally across the image 202 to indicate to the user which band each portion of the image 202 corresponds to. If the selected point 308 is dragged "upward" on the user interface in a first direction 224, the contrast of the entire image 202 is increased. If the selected point 308 is dragged downward on the user interface 112 in a second direction 226 the contrast of the entire image 202 is decreased. If the selected point 308 is dragged to the left in a third direction 228, the time gain compensation of band 215 is decreased. If the selected point 308 is dragged to the right in a fourth direction 230, the time gain compensation of band 215 is increased. In this example, the selected point 308 was dragged to the right in the fourth direction 230 and a portion 332 of the image 202 that corresponds to band 215 is displayed with an increased time gain compensation. Once the time gain compensation has been adjusted for a particular band, a different band (or the same band) can be selected in the time gain compensation can be adjusted.

Figure 4:
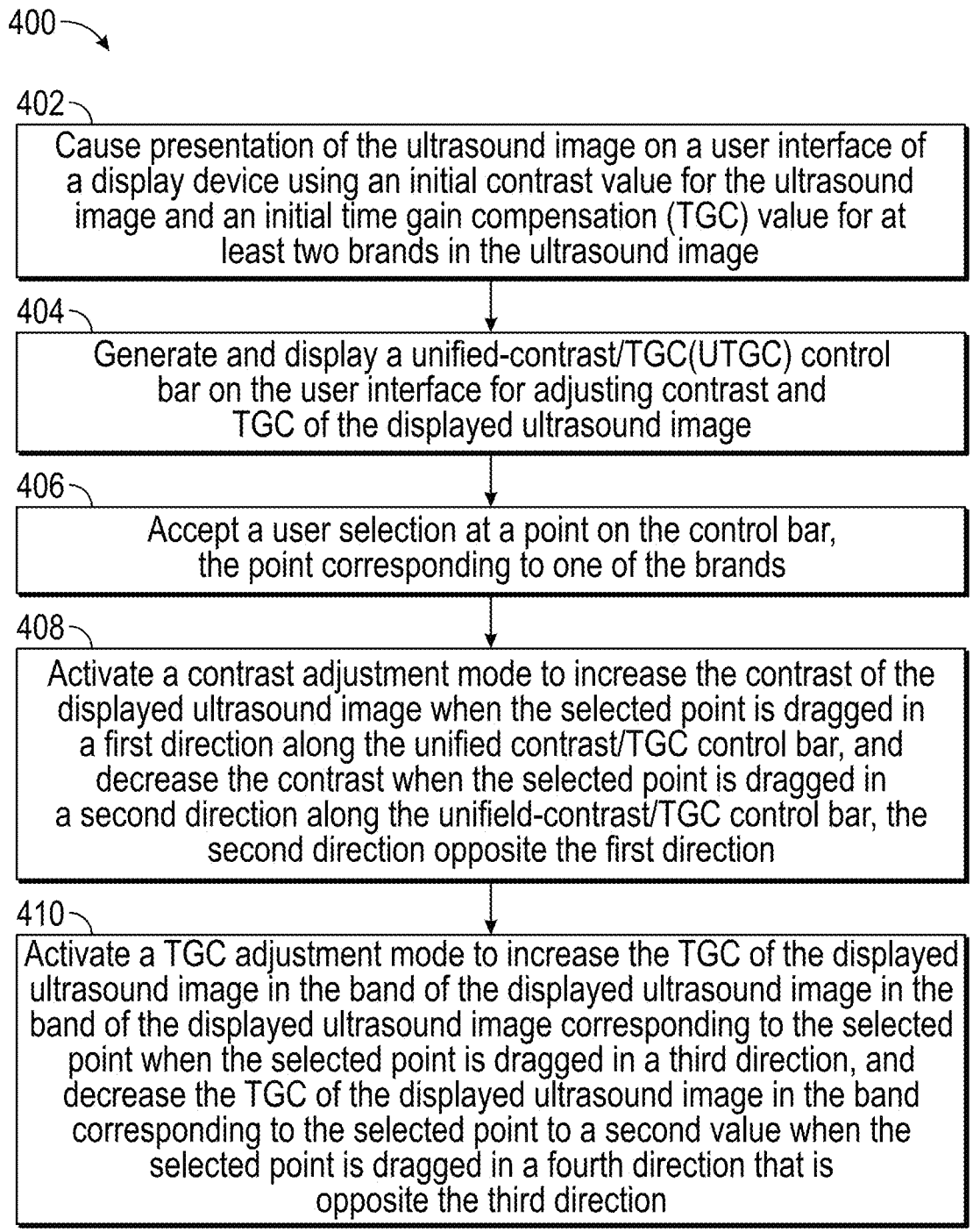
FIG. 4 is a flowchart illustrating a method for displaying a unified contrast and time gain compensation control bar.

FIG. 4 is a flowchart illustrating a process 400 for displaying a unified contrast and time gain compensation control bar. The method can be performed, for example, on the processing system 110 illustrated in FIG. 1. As described in reference to FIG. 1, ultrasound images are received by a processing system. At block 402, the method 400 begins, causing presentation of the ultrasound image on a user interface of a display device using an initial contrast value for the ultrasound image and an initial time gain compensation (TGC) value for at least two bands in the ultrasound image. Each band has a certain width and corresponds to a portion of the displayed ultrasound image that includes ultrasound information in a range of "depths" of the image. At block 404 the method 400 continues, generating and displaying a unified-contrast/TGC (UTGC) control bar on the user interface for adjusting contrast and TGC of the displayed ultrasound image. The UTGC control bar can be displayed adjacent to the ultrasound image on the left-hand side or the right-hand side of the user interface. Optionally, gridlines corresponding to the of these two bands can be displayed across the ultrasound image and indications of the bands can also appear on the UTGC controller (e.g., as indentations or another visible feature).

At block 406, the method can continue accepting a user selection at a point on the control bar, the point corresponding to one of the bands. An example of a point selection on the UTGC control bar is illustrated in FIG. 2 and FIG. 3. At block 408 the method can continue activating a contrast adjustment mode to increase the contrast of the displayed ultrasound image when the selected point is dragged in a first direction along the unified contrast/TGC control bar, and decrease the contrast when the selected point is dragged in a second direction along the unified-contrast/TGC control bar, the second direction opposite the first direction. In some embodiments, contrast can be increased by dragging the point upward on the user interface, and contrast can be decreased by dragging the point downward on the user interface. In other embodiments, contrast can be increased by dragging the point downward on the user interface, and contrast can be decreased by dragging the point upward on the user interface.

At block 410, the method 400 can continue activating a TGC adjustment mode to increase the TGC of the displayed ultrasound image in the band of the displayed ultrasound image corresponding to the selected point when the selected point is dragged in a third direction, and decrease the TGC of the displayed ultrasound image in the band corresponding to the selected point to a second value when the selected point is dragged in a fourth direction that is opposite the third direction. In some embodiments, the third direction can be to the left relative to the user interface and the fourth direction can be to the right relative to the user interface. In other embodiments, the third direction can be to the right relative to the user interface the fourth direction can be to the left relative to the user interface. Various examples of such methods can include any of the functionality and/or operations described herein.

Figure 5:
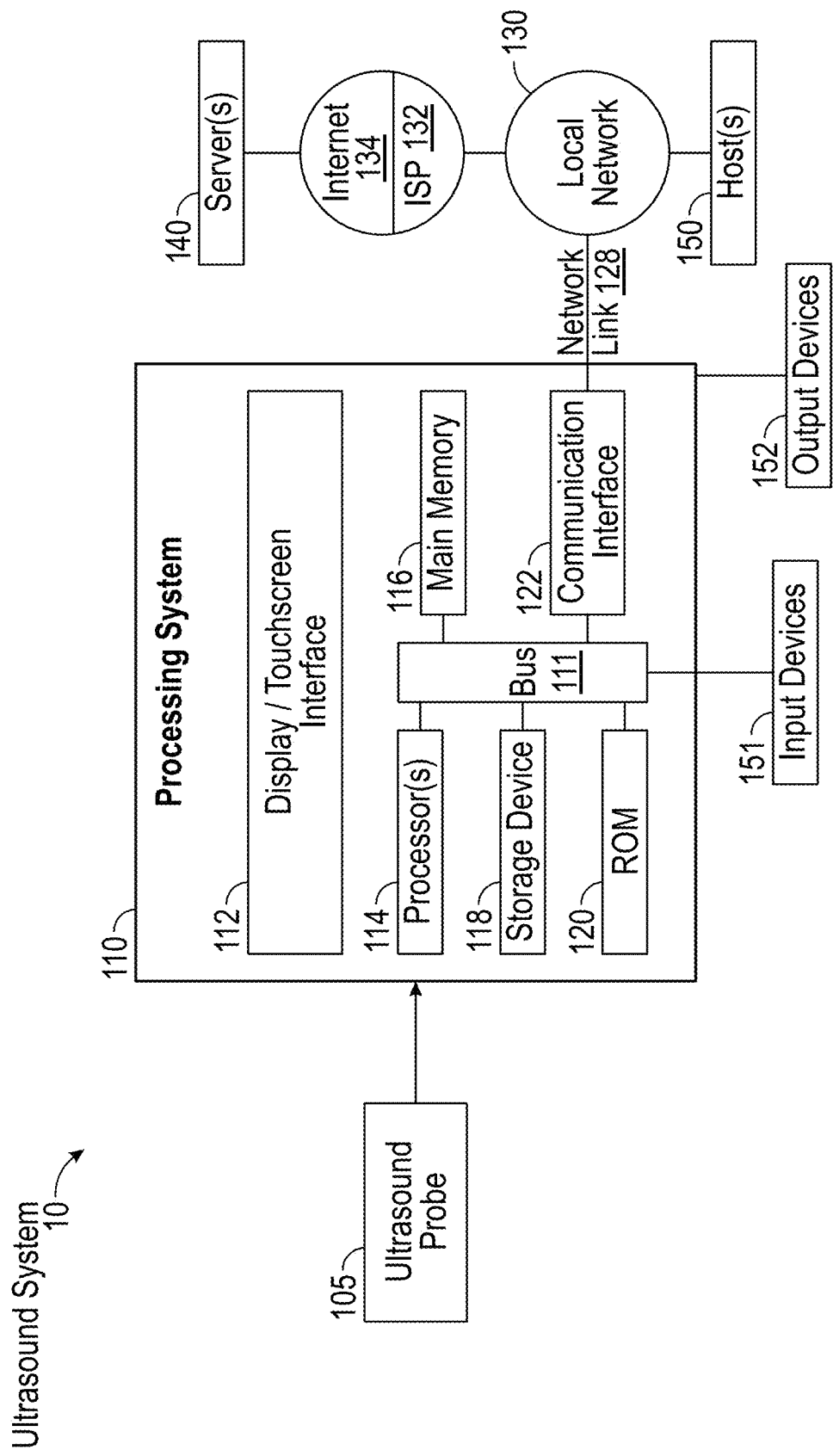
FIG. 5 is a block diagram illustrating an example of an ultrasound system that is adapted to perform functionality described herein.

FIG. 5 is a block diagram illustrating an example of an ultrasound system 10 that is adapted to perform functionality described herein relating to causing presentation of the ultrasound image on a user interface of a display 112 using an initial contrast value for the ultrasound image and an initial time gain compensation (TGC) value for at least two bands in the ultrasound image, and generating and cause displaying a unified contrast/TGC (UTGC) control bar on the user interface for adjusting contrast and TGC of the displayed ultrasound image. As illustrated in FIG. 5, the ultrasound system 10 includes an ultrasound probe 105 in communication with the processing system (computer system) 110. The ultrasound probe 105 can be connected to the computer system 110 via a wired or a wireless connection that allows the ultrasound probe 105 to provide ultrasound images to the computer system 110, and allows the ultrasound probe 105 to receive control signals from the computer system 110 the control signals indicating how ultrasound images should be collected.

The computer system 110 includes a bus 111 or other communication mechanism for communicating information, and a hardware processor (or multiple processors) 114 coupled with bus 111 for processing information. Hardware processor(s) 114 may be, for example, one or more general purpose microprocessors.

Computer system 110 also includes a main memory 116, such as a random access memory (RAM), cache and/or other dynamic storage devices, coupled to bus 111 for storing instructions to be executed by processor 114. Main memory 116 also may be used for storing temporary variables or other intermediate information during execution of instructions to be executed by processor 114. Such instructions, when stored in storage media accessible to processor 114, render computer system 110 into a special-purpose machine that is customized to perform the operations specified in the instructions. The main memory 116 may, for example, include instructions to display and use a UTGC control bar to easily and quickly adjust both the contrast of the displayed ultrasound image and the time gain compensation in different portions of the image, such that different portions (e.g., bands relating to the distance from the ultrasound probe) can have different time gain compensation adjustments.

Computer system 110 further includes a read only memory (ROM) 120 or other static storage device coupled to bus 111 for storing static information and instructions for processor 114. A storage device 118, such as a SSD drive, magnetic disk, optical disk, or USB thumb drive (Flash drive), etc., is provided and coupled to bus 111 for storing information and instructions.

The computer system 110 may be coupled via bus 111 to a display 112 (for example, a touch screen) for displaying information to a computer user. One or more input devices 151 which may include alphanumeric and other keys and/or provide cursor control (e.g., mouse, trackball, or cursor direction keys) for communicating direction information and command selections to processor 114 and for controlling cursor movement on display 112 can be coupled to bus 111 for communicating information and command selections to processor 114.

Computer system 110 may include a user interface module to implement a GUI that may be stored in a mass storage device as computer executable program instructions that are executed by the computing device(s). Computer system 110 may further, as described below, implement the techniques described herein using customized hard-wired logic, one or more ASICs or FPGAs, firmware and/or program logic which in combination with the computer system causes or programs computer system 110 to be a special-purpose machine. According to one embodiment, the techniques herein are performed by computer system 110 in response to processor(s) 114 executing one or more sequences of one or more computer readable program instructions contained in main memory 116. Such instructions may be read into main memory 116 from another storage medium, such as storage device 118. Execution of the sequences of instructions contained in main memory 116 causes processor(s) 114 to perform the process steps described herein. In alternative embodiments, hard-wired circuitry may be used in place of, or in combination with, software instructions.

Various forms of computer readable storage media may be involved in carrying one or more sequences of one or more computer readable program instructions to processor 114 for execution. For example, the instructions may initially be carried on a magnetic disk or solid state drive of a remote computer. The remote computer can load the instructions into its dynamic memory and send the instructions over a network link 128. Bus 111 carries the data to main memory 116, from which processor 114 retrieves and executes the instructions. The instructions received by main memory 116 may optionally be stored on storage device 118 either before or after execution by processor 114.

Computer system 110 also includes a communication interface 122 coupled to bus 111. Communication interface 122 provides a two-way data communication coupling to the network link 128 that is connected to a local network 130. For example, communication interface 122 may be an integrated services digital network (ISDN) card, cable modem, satellite modem, or a modem to provide a data communication connection to a corresponding type of telephone line. As another example, communication interface 122 may be a local area network (LAN) card to provide a data communication connection to a compatible LAN (or WAN component to communicate with a WAN). Wireless links may also be implemented. In any such implementation, communication interface 122 sends and receives electrical, electromagnetic or optical signals that carry digital data streams representing various types of information.

Network link 128 typically provides data communication through one or more networks to other data devices. For example, network link 128 may provide a connection through local network 130 to a host computer 150 or to data equipment operated by an Internet Service Provider (ISP) 132. ISP 132 in turn provides data communication services through the world wide packet data communication network now commonly referred to as the "Internet" 134. Local network 130 and Internet 134 both use electrical, electromagnetic or optical signals that carry digital data streams. The signals through the various networks and the signals on network link 128 and through communication interface 122, which carry the digital data to and from computer system 110, are example forms of transmission media. Computer system 110 can send messages and receive data, including program code, through the network(s), network link 128 and communication interface 122. In the Internet example, a server 140 might transmit a requested code for an application program through Internet 134, ISP 132, local network 130, the network link 128, and communication interface 122. The received code may be executed by processor 114 as it is received, and/or stored in storage device 118, or other non-volatile storage for later execution.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. For example, the software instructions may be executed to cause presentation of the ultrasound image on a user interface of a display device using an initial contrast value for the ultrasound image and an initial time gain compensation value for multiple bands in the ultrasound image, wherein each band is a portion of the displayed ultrasound image corresponding to a range of distances from an ultrasound scanner that generated the ultrasound image, and generate and display a unified-contrast/TGC (UTGC) control bar on the user interface for adjusting contrast and TGC of the displayed ultrasound image. The software instructions can also be executed to accept a user selection at a point on the control bar, the point corresponding to one of the bands, activate a contrast adjustment mode to increase the contrast of the displayed ultrasound image when the selected point is dragged in a first direction along the unified contrast/TGC control bar, and decrease the contrast when the selected point is dragged in a second direction along the unified-contrast/TGC control bar. The software instructions can also be executed to perform TGC adjustment mode to increase the TGC of the displayed ultrasound image in the band of the displayed ultrasound image corresponding to the selected point when the selected point is dragged in a third direction (e.g., laterally across the UTGC control bar) and decrease the TGC of the displayed ultrasound image in the band corresponding to the selected point when the selected point is dragged in a fourth direction that is opposite the third direction. The software instructions and/or other executable code may be read from a computer readable storage medium (or mediums). The software instructions and/or other executable code may be read from a computer readable storage medium (or mediums).

Computer readable program instructions described herein can be downloaded to a computing/processing device (e.g., a processing system 110) from a computer readable storage medium, an external computer, or an external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each device can receive computer readable program instructions from the network and forward the computer readable program instructions for storage in a computer readable storage medium within the respective device.

Implementation Considerations

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude non-transitory machine memories comprising software and thereby forming configurations of matter). Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory. In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

One or more aspects or features of the subject matter disclosed or claimed herein (e.g., processes and methods) may be realized in digital electronic circuitry, integrated circuitry, specially designed application specific integrated circuits (ASICs), field programmable gate arrays (FPGAs) computer hardware, firmware, software, and/or combinations thereof. These various aspects or features may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server may be remote from each other and may interact through a communication network. The relationship of client and server arises by virtue of computer programs running on the respective computers and having a client-server relationship to each other.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium.

In some embodiments, to provide for interaction with a user, one or more aspects or features of the subject matter described herein may be implemented on a computer having a display device for displaying information to the user, and an input interface by which the user may provide input to the computer. Other kinds of devices may be used to provide for interaction with a user as well. Other possible input devices include touch screens or other touch-sensitive devices such as single or multi-point resistive or capacitive trackpads, voice recognition hardware and software, and the like.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways.

As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

The computer program product may include a computer readable storage medium (or mediums) having computer readable program instructions thereon for causing a processor to carry out aspects of the present disclosure. The computer readable storage medium can be a tangible device that can retain and store data and/or instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Computer readable program instructions, may as also referred to herein as, for example, "code," "instructions," "module," "application," "software application," and/or the like. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device.

Aspects of the present disclosure are described herein with reference to methods, apparatus (systems), and computer program products according to embodiments of the disclosure. It will be understood that each method can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks. Any of the above-mentioned processors, and/or devices incorporating any of the above-mentioned processors, may be referred to herein as, for example, "computers," "computer devices," "computing devices," "hardware computing devices," "hardware processors," "processing units," and/or the like.

It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

EXAMPLE EMBODIMENTS

The following are certain examples of embodiments of the invention, which are not meant to be limiting in any way. In other words, other embodiments may include other combinations of features described in this disclosure.

Embodiment A: A system comprising a first non-transitory computer storage medium configured to store an ultrasound image; a second non-transitory computer storage medium configured to at least store computer-executable instructions; and one or more computer hardware processors in communication with the second non-transitory computer storage medium, the one or more computer hardware processors configured to execute the computer-executable instructions to at least: cause presentation of the ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image; and generate and cause presentation of a unified-contrast/TGC (UTGC) control bar on the user interface for adjusting contrast and TGC of the displayed ultrasound image, wherein the user interface is configured to accept a user input to adjust the TGC value of each of the at least two bands individually.

Embodiment B: The system of claim A, wherein the user interface is further configured to: accept a user selection at a point on the control bar, the point corresponding to one of the bands, activate a contrast adjustment mode to increase the contrast of the displayed ultrasound image when the selected point is dragged in a first direction along the unified contrast/TGC control bar, and decrease the contrast when the selected point is dragged in a second direction along the unified-contrast/TGC control bar, the second direction opposite the first direction; and activate a TGC adjustment mode to increase the TGC of the displayed ultrasound image in the band of the displayed ultrasound image corresponding to the selected point when the selected point is dragged in a third direction, and decrease the TGC of the displayed ultrasound image in the band corresponding to the selected point to a second value when the selected point is dragged in a fourth direction that is opposite the third direction.

Embodiment C: The system of embodiment B, wherein the third direction is substantially orthogonal to the first direction, and the fourth direction is substantially orthogonal to the first direction.

Embodiment D: The system of embodiment B, wherein the one or more computer hardware processors are further configured to execute the computer-executable instructions to store contrast and TGC information for the ultrasound image after the contrast and TGC have been adjusted such that the contrast and TGC information can be subsequently used for displaying the ultrasound image.

Embodiment E: The system of embodiment B, wherein dragging the user selection in the first and second direction from any band adjusts the contrast of the entire image.

Embodiment F: The system of embodiment B, wherein the one or more computer hardware processors are further configured to execute the computer-executable instructions to configure the user interface to not display the UTGC control bar when in a hidden mode, and to display the unified contrast/TGC control bar in response to a selection, wherein the selection is an input on the display corresponding to the location of the hidden contrast/TGC control bar, or the selection is an input from a menu or button on the user interface.

Embodiment G: The system of embodiment A, wherein the UTGC control bar is presented in the hidden-mode on the right edge of the user interface.

Embodiment H: The system of either of embodiment G, wherein the right edge of the user interface corresponds to a portion of the user interface within 25% of the right side of the user interface.

Embodiment I: The system of embodiment A, wherein the UTGC control bar is presented in the hidden-mode on the left edge of the user interface.

Embodiment J: The system of either of embodiment I, wherein the left edge of the user interface corresponds to a portion of the user interface within 25% of the left side of the user interface.

Embodiment K: The system of embodiment A, wherein the one or more computer hardware processors are further configured to execute the computer-executable instructions to hide the unified contrast/TGC control bar during ultrasound scanning.

Embodiment L: The system of any one of embodiments A-K, wherein the UTGC control bar contains UTGC boxes which correspond to the TGC bands of the image, wherein the shade of the box represents the effect of both contrast and TGC on the portion of the image in a band.

Embodiment M: The system of embodiment L, wherein the one or more computer hardware processors are further configured to execute the computer-executable instructions such that the UTGC boxes are zoom and pan sensitive, that is they align correctly when the image is zoomed or panned.

Embodiment N: The system of any one of embodiments A-M, wherein the one or more computer hardware processors are further configured to execute the computer-executable instructions to generate and present on the user interface a contrast icon that indicates a digital value of the contrast.

Embodiment O: The system of any one of embodiments B-N, wherein the one or more computer hardware processors are further configured to execute the computer-executable instructions such the user interface is configured such that while the contrast is being adjusted, TGC adjustment does not occur.

Embodiment P: The system of embodiment 14, wherein the one or more computer hardware processors are further configured to execute the computer-executable instructions to reset the contrast to a default value by double-tapping the contrast icon.

Embodiment Q: The system of embodiment 2, wherein the third direction is left and the fourth direction is right, relative to the user interface.

Embodiment R: The system of embodiment 2, wherein the third direction is right and the fourth direction is left, relative to the user interface.

Embodiment S: The system of claim 19 or 20, wherein the UTGC bar includes a box that corresponds to each band, and dragging left and right in a box that corresponds to the selected point adjusts TGC for the band corresponding to the box.

Embodiment T: The system of embodiment 21, wherein the one or more computer hardware processors are further configured to execute the computer-executable instructions to adjust the TGC only for the band corresponding to the box of the selected point.

Embodiment U: The system of embodiment 21, wherein the one or more computer hardware processors are further configured to execute the computer-executable instructions such that if the user selected point is dragged to a second box, the TGC corresponding to the second box will be adjusted.

Embodiment V: The system of embodiment 1, wherein the one or more computer hardware processors are further configured to execute the computer-executable instructions to generate and display horizontal grid lines for all TGC bands when adjusting the TGC for any of the bands.

Embodiment W: The system of embodiment 1, wherein the one or more computer hardware processors are further configured to execute the computer-executable instructions to generate and display a TGC a numerical value for the adjustment on the box for each band when the TGC is adjusted.

Embodiment X: The system of embodiment 1, wherein the one or more computer hardware processors are further configured to execute the computer-executable instructions to reset a specific TGC band, displayed in the user interface, to a default value by double-tapping a location on the control bar corresponding to the specific TGC band.

Embodiment Y: The system of embodiment 1, wherein the one or more computer hardware processors are further configured to execute the computer-executable instructions such that once the user stops dragging by unclicking or untouching, the UTGC control bar remains displayed for a duration of five seconds or less and then disappears.

Embodiment Z: The system of embodiment 1, wherein the one or more computer hardware processors are further configured to execute the computer-executable instructions to enter a contrast mode or a TGC mode immediately after when touching the UTGC control bar area without waiting for the UTGC control bar to appear.

Embodiment AA: The system of embodiment 1, wherein the one or more computer hardware processors are further configured to execute the computer-executable instructions to animate both the appearance and disappearance of the UTGC control bar.

Embodiment AB: The system of embodiment 1, wherein the one or more computer hardware processors are further configured to execute the computer-executable instructions to control the number and spacing of the TGC bands by receiving an input through the user interface of a number of bands or of a band spacing.

Embodiment AC: A method of controlling contrast and time gain compensation using a unified control, the method comprising: causing presentation of an ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image; and generating and displaying a unified-contrast/TGC (UTGC) control bar on the user interface for adjusting contrast and TGC of the displayed ultrasound image.

Embodiment AD: The method of embodiment AC, further comprising accepting a user selection at a point on the control bar, the point corresponding to one of the bands, activating a contrast adjustment mode to increase the contrast of the displayed ultrasound image when the selected point is dragged in a first direction along the UTGC control bar, and decrease the contrast when the selected point is dragged in a second direction along the unified-contrast/TGC control bar, the second direction opposite the first direction; and activating a TGC adjustment mode to increase the TGC of the displayed ultrasound image in the band of the displayed ultrasound image corresponding to the selected point when the selected point is dragged in a third direction, and decrease the TGC of the displayed ultrasound image in the band corresponding to the selected point to a second value when the selected point is dragged in a fourth direction that is opposite the third direction.

Embodiment AE: The method of embodiment AD, wherein the third direction is substantially orthogonal to the first direction, and the fourth direction is substantially orthogonal to the first direction.

Embodiment AF: The method of any one of embodiments AC-AE, further comprising storing contrast and TGC information for the ultrasound image after the contrast and TGC have been adjusted such that the contrast and TGC information can be subsequently used for displaying the ultrasound image.

Embodiment AG: The method of any one of embodiments AC-AF, further comprising dragging the user selection in the first and second direction starting from any band to adjust contrast of all the bands.

Embodiment AH: The method of any one of embodiments AC-AG, further comprising presenting the unified contrast/TGC (UTCG) control bar in a hidden-mode that is not visible on the display, and display the control bar in response to a pointing device selection on the display at a location corresponding to the hidden UTCG control bar.

Embodiment AI: The method of embodiment AC, further comprising presenting the UTGC control bar in the hidden-mode on the right edge of the user interface.

Embodiment AJ: The method of either of embodiment AI, wherein the right edge of the user interface corresponds to a portion of the user interface within 25% of the right side of the user interface.

Embodiment AK: The method of embodiment AC, further comprising presenting the unified contrast/TGC control bar in the hidden-mode on the left edge of the user interface.

Embodiment AL: The method of embodiment AK, wherein the left edge of the user interface corresponds to a portion of the user interface within 25% of the left side of the user interface.

Embodiment AM: The method of any one of embodiments AC-AL, further comprising hiding the UTGC control bar during ultrasound scanning.

Embodiment AN: The method of any one of embodiments AC-AL, wherein the user interface is configured to display the UTGC control bar such that it contains grayscale boxes which correspond to the TGC bands of the image, wherein the shade of the box represents the effect of both contrast and TGC on the portion of the image in a band.

Embodiment AO: The method of embodiment AN, wherein the UTGC control bar grayscale boxes are zoom and pan sensitive, that is they align correctly when the image is zoomed or panned.

Embodiment AP: The method of any one of embodiments AC-AO, wherein the user interface is configured to adjust an image display parameter of all of the bands simultaneously.

Embodiment AQ: The method of embodiment any of embodiments AC-AP, further comprising generating and presenting on the user interface a contrast icon that indicates a digital value of the contrast.

Embodiment AT: The method of embodiment AC, further comprising resetting the contrast to a default value by double-tapping the contrast icon in the user interface.

Embodiment AU: The method of embodiment AC, wherein the third direction is left and the fourth direction is right, relative to the user interface.

Embodiment AV: The method of embodiment AC, wherein the third direction is right and the fourth direction is left, relative to the user interface.

Embodiment AW: The method of any one of embodiments AC-AV, wherein the UTGC bar includes a box that corresponds to each band, and dragging a selected point left or right in a box adjusts TGC for the band corresponding to the box.

Embodiment AZ: The method of one of embodiments AC-AW, further comprising generating and displaying horizontal grid lines for all TGC bands when the user interface is used to adjust the TGC for any of the bands.

Embodiment BA: The method of any one of AC-AZ, further comprising generating and displaying on the user interface a TGC numerical value for a band when the TGC is adjusted.

Embodiment BB: The method of any one of AC-BA, further comprising resetting each TGC band to a default value by double-tapping a control icon displayed on the user interface.

Embodiment BC: The method of any one of AC-BB, further comprising displaying the UTGC control bar on the user interface for a duration of five seconds or less and once the user stops interacting with the UTGC control bar (e.g., by unclicking or un-touching the UTGC control bar).

Embodiment BD: The method of any one of AC-BC, further comprising entering a contrast mode or a TGC mode on the user interface immediately after touching the UTGC control bar area without waiting for the UTGC control bar to appear.

Embodiment BE: The method of embodiment BC or BD, further comprising animating both the appearance and disappearance of the UTGC control bar.

Embodiment BF: The method of any one of embodiments AC-BE, further comprising receiving a band number input via the user interface and setting the number of bands on the displayed imaged on the user interface based on the band number input.

Embodiment BG: The method of any one of embodiments AC-BE, further comprising receiving a band spacing input through the user interface and setting the band spacing on the user interface based on the received input.

The disclosed technology has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A system comprising:
    a first non-transitory computer storage medium configured to store an ultrasound image;
    a second non-transitory computer storage medium configured to at least store computer-executable instructions; and
    one or more computer hardware processors in communication with the second non-transitory computer storage medium, the one or more computer hardware processors configured to execute the computer-executable instructions to at least:
       cause presentation of the ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image; and
       generate and cause presentation of a unified contrast/TGC (UTGC) control bar on the user interface for adjusting contrast and TGC of the displayed ultrasound image, wherein the user interface is configured to accept a user selection at a point on the control bar, the point corresponding to one of the at least two bands;
       activate a contrast adjustment mode to adjust the contrast of the displayed ultrasound image when the selected point is dragged in a first or second direction along the UTGC control bar; and
       activate a TGC adjustment mode to adjust the TGC of the displayed ultrasound image in one of the at least two bands of the displayed ultrasound image corresponding to the selected point when the selected point is dragged in a third or fourth direction.

2. The system of claim 1, wherein the one or more computer hardware processors are further configured to execute the computer-executable instructions to store contrast and TGC information for the ultrasound image after the contrast and TGC have been adjusted such that the contrast and TGC information can be subsequently used for displaying the ultrasound image.

3. The system of claim 1, wherein the one or more computer hardware processors are further configured to execute the computer-executable instructions to configure the user interface to not visibly display the UTGC control bar on the user interface when in a hidden mode, and to display the unified contrast/TGC control bar in response to a selection, wherein the selection is an input on the display corresponding to the location of the hidden contrast/TGC control bar or the selection is an input from a menu or button on the user interface.

4. The system of claim 1, wherein the UTGC control bar is located in the user interface on the right edge or the left edge of the user interface, wherein the right edge of the user interface corresponds to a portion of the user interface within 25% of the right side of the user interface, and the left edge corresponds to a portion of the user interface within 25% of the left side of the user interface.

5. The system of claim 1, wherein the one or more computer hardware processors are further configured to execute the computer-executable instructions to hide the unified contrast/TGC control bar during ultrasound scanning.

6. The system of claim 1, wherein the one or more computer hardware processors are further configured to execute the computer-executable instructions to generate and present, on the user interface, a contrast icon that indicates a digital value of the contrast of the displayed ultrasound image and a TGC numerical value indicting a TGC value corresponding to one of the at least two bands.

7. The system of claim 1, wherein the one or more computer hardware processors are further configured to execute the computer-executable instructions to generate and display on the user interface horizontal grid lines indicative of each of the at least two bands.

8. The system of claim 1, wherein the UTGC control bar contains a first UTGC box and a second UTGC box both of which correspond to the at least two bands of the image, wherein the depiction of the first box represents an effect of both contrast and TGC on the portion of the image in one of the at least two bands and the depiction of the second box represents an effect of TGC on the portion of the image in the same band.

9. The system of claim 8, wherein the one or more computer hardware processors are further configured to execute the computer-executable instructions to configure the user interface to generate and present the first and second UTGC boxes to be zoom and pan sensitive such that they align correctly when the displayed ultrasound image is zoomed or panned.

10. A method, comprising:
    causing presentation of an ultrasound image on a user interface of a display device using an initial contrast value for the ultrasound image and an initial time gain compensation (TGC) value for at least two bands in the ultrasound image, each band being a portion of the displayed ultrasound image corresponding to a range of distances from an ultrasound scanner that generated the ultrasound image; and
    generating and displaying a unified-contrast/TGC (UTGC) control bar on the user interface for adjusting contrast and TGC of the displayed ultrasound image;
    activating a contrast adjustment mode to adjust the contrast of the displayed ultrasound image when the selected point is dragged in a first or second direction along the UTGC control bar; and
    activating a TGC adjustment mode to adjust the TGC of the displayed ultrasound image in one of the at least two bands of the displayed ultrasound image corresponding to the selected point when the selected point is dragged in a third or fourth direction, wherein the method is performed by one or more computer hardware processors executing computer-executable instructions stored on a non-transitory computer storage medium.

11. The method of claim 10, wherein the one or more computer hardware processors are further configured to execute the computer-executable instructions to store contrast and TGC information for the ultrasound image after the contrast and TGC have been adjusted such that the contrast and TGC information can be subsequently used for displaying the ultrasound image.

12. The method of claim 10, wherein generating and displaying a unified-contrast/TGC (UTGC) control bar on the user interface comprises displaying the UTGC control bar when in a non-hidden mode and not visibly displaying the UTGC control bar when in a hidden mode, and wherein the method further comprises displaying the UTGC control bar in a non-hidden mode in response to a user input.

13. The method of claim 10, wherein the UTGC control bar is displayed in the user interface on the right edge or the left edge of the user interface, wherein the right edge of the user interface corresponds to a portion of the user interface within 25% of the right side of the user interface, and the left edge corresponds to a portion of the user interface within 25% of the left side of the user interface.

14. The method of claim 10, further comprising hiding the unified contrast/TGC control bar during ultrasound scanning.

15. The method of claim 10, further comprising generating and displaying on the user interface, a contrast icon that indicates a digital value of the contrast of the displayed ultrasound image and a TGC numerical value indicting a TGC value corresponding to one of the at least two bands TGC band.

16. The method of claim 10, further comprising generating and displaying, on the user, interface horizontal grid lines indicative of each of the at least two bands.

17. The method of claim 10, wherein the UTGC control bar includes a first UTGC box and a second UTGC box both of which correspond to the at least two bands of the image, wherein the depiction of the first box on the user interface represents an effect of contrast on the portion of the image in one of the at least two bands and the depiction of the second box represents an effect of TGC on the portion of the image in the same band.

18. The method of claim 17, further comprising generating and presenting the user interface to generate and present the first and second UTGC boxes to be zoom and pan sensitive such they align correctly when the displayed ultrasound image is zoomed or panned.

* * * * *